United States Patent [19]

Fournier et al.

[11] Patent Number: 5,254,468
[45] Date of Patent: Oct. 19, 1993

[54] BILAYER PELLET CONTAINING IMMOBILIZED XYLOSE ISOMERASE AND UREASE FOR THE SIMULTANEOUS ISOMERIZATION AND FERMENTATION OF XYLOSE TO ETHANOL

[75] Inventors: Ronald L. Fournier; Sasidhar Varanasi; James P. Byers, all of Toledo, Ohio

[73] Assignee: The University of Toledo, Toledo, Ohio

[21] Appl. No.: 785,938

[22] Filed: Oct. 31, 1991

[51] Int. Cl.$^5$ .......................... C12P 7/14; C12P 19/24; C12N 11/18; C12N 11/04
[52] U.S. Cl. ...................................... 435/162; 435/94; 435/161; 435/175; 435/180; 435/182
[58] Field of Search ................. 435/94, 175, 180, 182, 435/161, 162

[56] References Cited

U.S. PATENT DOCUMENTS 4,490,468 12/1984 Gong et al. .......................... 435/161
4,506,015 3/1985 Ho et al. .............................. 435/175

FOREIGN PATENT DOCUMENTS 0048080 3/1984 Japan .................................... 435/175

Primary Examiner—David M. Naff
Attorney, Agent, or Firm—Marshall & Melhorn

[57] ABSTRACT

A bilayered immobilized enzyme pellet and a process to manufacture this pellet are provided for use in a process involving the simultaneous isomerization of xylose to xylulose and fermentation of xylulose to ethanol. The bilayered pellet is able to maintain the environment where the isomerization reaction occurs within its optimum pH of 7.0 to 8.0 while the fermentation reaction occurs within its optimum pH range of 4.0 to 5.0. This process allows both xylose and glucose sugars to be effectively used as a feedstock for ethanol production by isomerizing the xylose to xylulose and then making the xylulose immediately available for the fermentation process. Because the xylose has been converted to its ketose isomer, xylulose, yeasts which can ferment glucose and xylulose can be used in this process.

7 Claims, 2 Drawing Sheets

BILAYER PELLET CONTAINING IMMOBILIZED XYLOSE ISOMERASE AND UREASE FOR THE SIMULTANEOUS ISOMERIZATION AND FERMENTATION OF XYLOSE TO ETHANOL

BACKGROUND OF THE INVENTION

The large scale production of ethanol has become increasingly important because of ethanol's use as a liquid fuel in gasoline additives and because it can be derived from renewable resources. Ethanol can be obtained from the anaerobic fermentation of simple sugars, however, the metabolic pathways by which yeasts are able to break down the sugar molecules differ as to the type of sugar fermented. Thus many strains of yeast which are able to ferment glucose and other six carbon sugars (hexoses) are unable to ferment xylose and other five carbon sugars (pentoses) because the metabolic pathway by which the pentose sugars are utilized is ineffective. Most yeasts are capable of fermenting glucose to ethanol in high yields, however, only a few yeast strains or yeast mutants have been identified as being able to directly ferment xylose. Thus, the production of ethanol by fermentation of simple sugars has been largely obtained from glucose and not xylose.

The source of the simple hexose sugars for fermentation into ethanol is typically cane sugar and starch containing grains. The use of cane sugar for fermentation into ethanol is economical only in countries where the climate is conducive to year round production and where there are low labor costs. Corn is predominantly used for this process in the United States, largely because of its availability and low price and the availability of tax credits for grain used for the production of ethanol. One alternate source that is starting to receive increased attention is lignocellulosic material, or alternatively referred to as biomass. Lignocellulose has great economic potential as a feed stock because large quantities of it can be readily obtained from agricultural residues, forest industry by-products, or paper industry waste. A disadvantage of lignocellulose as a feed stock for fermentation is that one of its three major components, hemicellulose, which comprises 20 to 30% of the lignocellulose, is predominantly composed of the biopolymer xylan whose monomer unit is xylose. Cellulose, the largest fraction of lignocellulose at 30 to 40% of the total material, is a biopolymer whose monomer unit is glucose. Thus, in order for lignocellulose to be an economical feed stock for ethanol production, both the xylose and glucose fractions must be fermented.

Although xylose is not directly fermentable by most yeasts, it is well known that its ketose isomer, xylulose, can be fermented by the same yeasts that are able to ferment glucose. The isomerization of xylose to xylulose can be accomplished with the catalyst xylose isomerase (also referred to as glucose isomerase or aldose isomerase). However, the proportion of xylose to xylulose in the reaction mixture when the enzymic isomerization reaches equilibrium is only about 5:1. High conversion rates of xylose can, therefore, be realized only by preventing the reaction from reaching equilibrium by continuously fermenting xylulose to ethanol as soon as it is formed. This latter goal can be achieved by conducting the isomerization and the fermentation steps concurrently in a single reactor.

The activity of the xylose isomerase is a very strong function of pH, with its optimum pH to be reported in the range of 7.0 to 8.0. However, unlike the isomerization reaction, the optimum pH of the fermentation reaction is between 4.0 and 5.0. Thus in order to optimize both the isomerization and fermentation process, it has been necessary to carry out these reactions in separate environments and at significantly different pH conditions. As an example, Gong et al., U.S. Pat. No. 4,490,468 discloses separate reactors for the isomerization and fermentation processes. This reference does disclose that these two processes could be performed simultaneously, but it does not propose any means or methods for maintaining the different optimum pH conditions for each reaction in a single reactor. In fact it proposes a compromised pH range of 6.8 to 8.0, preferably at 7.0 for both processes.

OBJECTS OF THE INVENTION

It is an object of this invention to provide a process for the simultaneous isomerization of xylose to xylulose and fermentation of xylulose to ethanol whereby each reaction occurs within its optimum pH environment by immobilizing xylose isomerase in a porous polymer material so as to form a particle, said particle forming an inner core region of a larger pellet, coating said particle with a porous polymer material and immobilizing urease in said porous polymer material, said coating forming the outer layer of said pellet, mixing xylose feedstock, urea, and yeast cells having a high ethanol productivity and ethanol tolerance so as to form a bulk liquid, said bulk liquid being placed in a closed reactor having agitation means, setting and adjusting the pH of the bulk liquid so as to maintain the pH in the range of 4.0 to 5.0, dispersing bilayered immobilized enzyme pellets in said bulk liquid, diffusing xylose into said inner core region of said pellet, isomerizing said diffused xylose to xylulose by contact with xylose isomerase immobilized in said inner core, diffusing said xylulose out into said bulk liquid, adjusting the pH of said inner core region so as to maintain the pH in the range of 7.0 to 8.0 by diffusing said urea in said bulk liquid into the outer layer of said pellet whereby the urea is hydrolyzed to ammonia by the immobilized enzyme urease, said ammonia neutralizing any hydrogen or positively charged ions that diffuse from said bulk liquid into said inner core region of said pellet, agitating said bilayered pellets and bulk liquid under largely anaerobic conditions and at temperatures sufficiently long so as to allow the fermentation of xylulose to ethanol, converting said xylulose to ethanol by fermentation contemporaneously with the isomerization of xylose to xylulose.

It is a further object of this invention to provide a process for the manufacture of a bilayered immobilized enzyme pellet for use in the above simultaneous isomerization and fermentation process by immobilizing xylose isomerase in a porous polymer material so as to form an inner core region of a particle, mixing said particles with urease, a monomer, a crosslinking agent, and a polymerization initiator so as to form an aqueous medium, said aqueous medium and particles comprising an aqueous suspension, maintaining said aqueous suspension at a temperature between 0° to 4° C., adding toluene, chloroform, and a surfactant so as to form a hydrophobic phase, agitating said hydrophobic phase under nitrogen conditions and at a temperature between 0° and 4° C., adding said aqueous suspension to said hydrophobic phase so as to allow a mixture of said monomer and urease to form a thin outer layer around said particles.

It is still a further object of this invention to provide a bilayered immobilized enzyme pellet which can maintain a pH gradient between the bulk liquid and the inner core region of this pellet so as to maintain the pH of the bulk liquid at the xylulose fermentation optimum pH range of 4.0 to 5.0 and to maintain the pH of the inner core region at the xylose isomerization optimum range of 7.0 to 8.0. This bilayered immobilized enzyme pellet is comprised of a core region of porous polymer material containing immobilized xylose isomerase and an outer layer of porous polymer material containing immobilized urease.

SUMMARY OF THE INVENTION

The present invention provides for the production of ethanol from the simultaneous processes of isomerization of xylose to xylulose and fermentation of xylulose to ethanol in a single reactor and in the presence of the yeast. Because the isomerization and fermentation processes require different pH conditions for optimum results, the present invention provides a bilayered immobilized enzyme pellet which is capable of maintain a pH gradient between the inner core of the pellet and the bulk liquid in the reactor. The bilayered pellet is comprised of an inner core region made from a porous polymer material and wherein the enzyme xylose isomerase is immobilized and an outer layer, also made from a porous polymer material, and which has the enzyme urease immobilized therein.

The process for producing ethanol starts with mixing this bilayered pellet with glucose and xylose feed stock, yeast, a buffer and urea in a reactor. The urease immobilized in the outer layer hydrolyzes the urea to ammonia which in turn neutralizes the hydrogen ions diffusing in from the bulk liquid toward the inner core region. Thus this outer layer maintains the pH in the inner core region between 7.0 to 8.0. These pH conditions in the presence of the enzyme xylose isomerase allows the xylose, which diffuses into the inner core region, to undergo isomerization to xylulose. When the xylulose diffuses back out to the bulk liquid, it will be immediately available to undergo the fermentation process in the bulk liquid where yeast and pH conditions of 4.0 to 5.0 are present.

DETAILED DESCRIPTION OF THE INVENTION

The production of ethanol from a fermentable source having both glucose and xylose as constituents is provided whereby a bilayered pellet is mixed with glucose and xylose feed stocks, urea, and yeast in a reactor equipped with agitation means, such as a continuously stirred tank reactor (CSTR). The process for the simultaneous isomerization and fermentation of xylose that is described within can be performed under both batch or continuous modes.

Figure 1A:
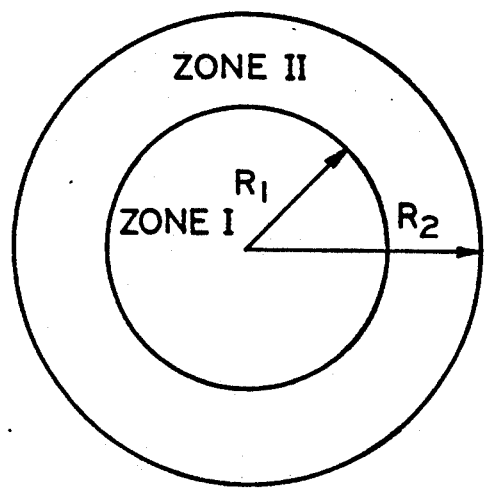
FIG. 1 is a schematic illustration of the bilayered pellet described herein.
Figure 1B:
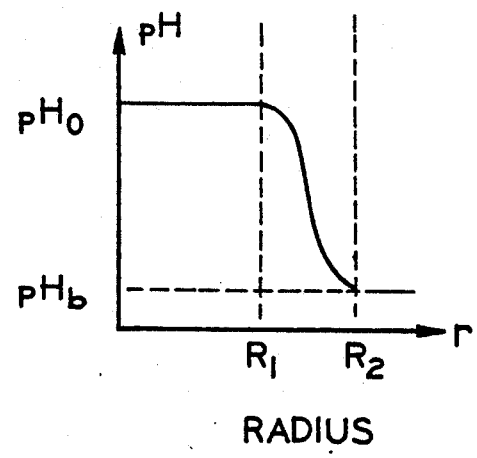

As seen from FIG. 1, the bilayered pellet is comprised of an inner core region designated as zone 1, and an outer layer designated as zone 2. Both zones of the pellet are made from a porous polymer material and have an enzyme immobilized within. The enzyme xylose isomerase is immobilized within zone 1 while the enzyme urease is immobilized within zone 2, as will be described further below.

It should be appreciated that the bilayered immobilized enzyme pellet of the present invention has potential in other enzymatic reactions as well because of its ability to sustain and control a pH gradient. Therefore, pellets having different enzymes immobilized within the inner core region and outer layer could be used depending on the application of the pellet. Examples include the production of penicillinic acid as well as the controlled-release of insulin in the treatment of diabetes mellitus where changes in plasma glucose levels can be used with immobilized glucose oxidase to generate a pH gradient with a membrane thus affecting its permeability to insulin.

The bilayered immobilized enzyme pellet is produced by a combination of enzyme trapping techniques that are well known in the art. Zone 1 is manufactured first and can be made by suspension polymerization techniques used to entrap xylose isomerase in a suitable medium. Alternatively and preferably, a commercially prepared pellet having xylose isomerase immobilized within could be used. One such pellet which is suitable for this application is Sweetzyme ®T (manufactured by NOVO Nordisk Biolabs). The amount of xylose isomerase that is immobilized within zone 1 can vary based upon the amount of xylose isomerization that is desired. A non-ionic (neutral) or cationic polymer material is preferred for the enzyme entrapping medium because the choice of a neutral or cationic polymer material will not facilitate the diffusion of hydrogen ions into the pellet.

The preferred procedure for coating zone 1 and thus creating zone 2 of the pellet is derived by combining a suspension polymerization technique for preparing polyacrylamide beads containing entrapped enzymes with a technique for preparing double emulsions. The procedure consists of redispersing an aqueous suspension of zone 1 particles in a hydrophobic phase resulting in a double suspension. The aqueous suspension is comprised of an aqueous phase and zone 1 particles, which are dispersed within the aqueous phase. The aqueous phase contains dissolved urease, a monomer, such as acrylamide, a crosslinking agent, and a polymerization initiator. The polymerization takes place in situ in an aqueous film surrounding the zone i particles and results in a crosslinked polyacrylamide outer layer containing entrapped urease. The monomer acrylamide is chosen because it is non-ionic and because it is well understood in the art as to how to make an enzyme trapping gel from this monomer. Alternatively, any other non-ionic or cationic monomer could be used.

The hydrophobic phase is a mixture that is immiscible with water, volatile organic compounds, the mixture having a density similar to the aqueous phase. An example of an appropriate mixture is toluene and chloroform. A surfactant, such as Sorbitan sesquoleate is also added. This hydrophobic organic phase is placed in a closed reactor equipped with agitation means, a nitrogen source and associated inlet and outlet piping, and a isolable funnel for the admission of the aqueous suspension of zone 1 particles. The reactor is kept cold, preferably in the 0° to 4° C. range, and the hydrophobic phase is stirred under a nitrogen atmosphere.

The aqueous phase is prepared by mixing a monomer and a crosslinking agent, such as N,N'-methylenebisacrylamide (BIS) in a Tris-HCL buffer, having a pH of 7.3. Urease is then dissolved into this phase and zone 1 particles (such as Sweetzyme®T particles) are dispersed. The amount of urease that is required for the present invention is dependent on several other factors which will be discussed later. This aqueous solution is also maintained at 0° to 4° C.

The next step is to add the polymerization initiators, such as N, N,N', N'-tetramethylethylenediamine (TEMED) and ammonium persulphate. Next the aqueous suspension with the polymerization initiators is quickly added to the closed reactor containing the hydrophobic organic phase. Agitation, a nitrogen environment and a temperature of 0° to 4° C. is maintained throughout the polymerization. The polymerization process should proceed for approximately 30 minutes.

When the process is complete, the resulting particles are washed to remove the organic compounds. The bilayered, immobilized enzyme pellets should be kept at 0° to 4° C. until subsequent use.

It should be noted that the thickness of the urease layer formed around the zone particles can be controlled by controlling the agitation speed and the amount of the surfactant added to the hydrophobic phase. The thickness of the urease layer, as well as the amount of urease immobilized within zone 2 will effect how the pellet operates to maintain a pH gradient as discussed further.

EXAMPLE 1

Figure 2:
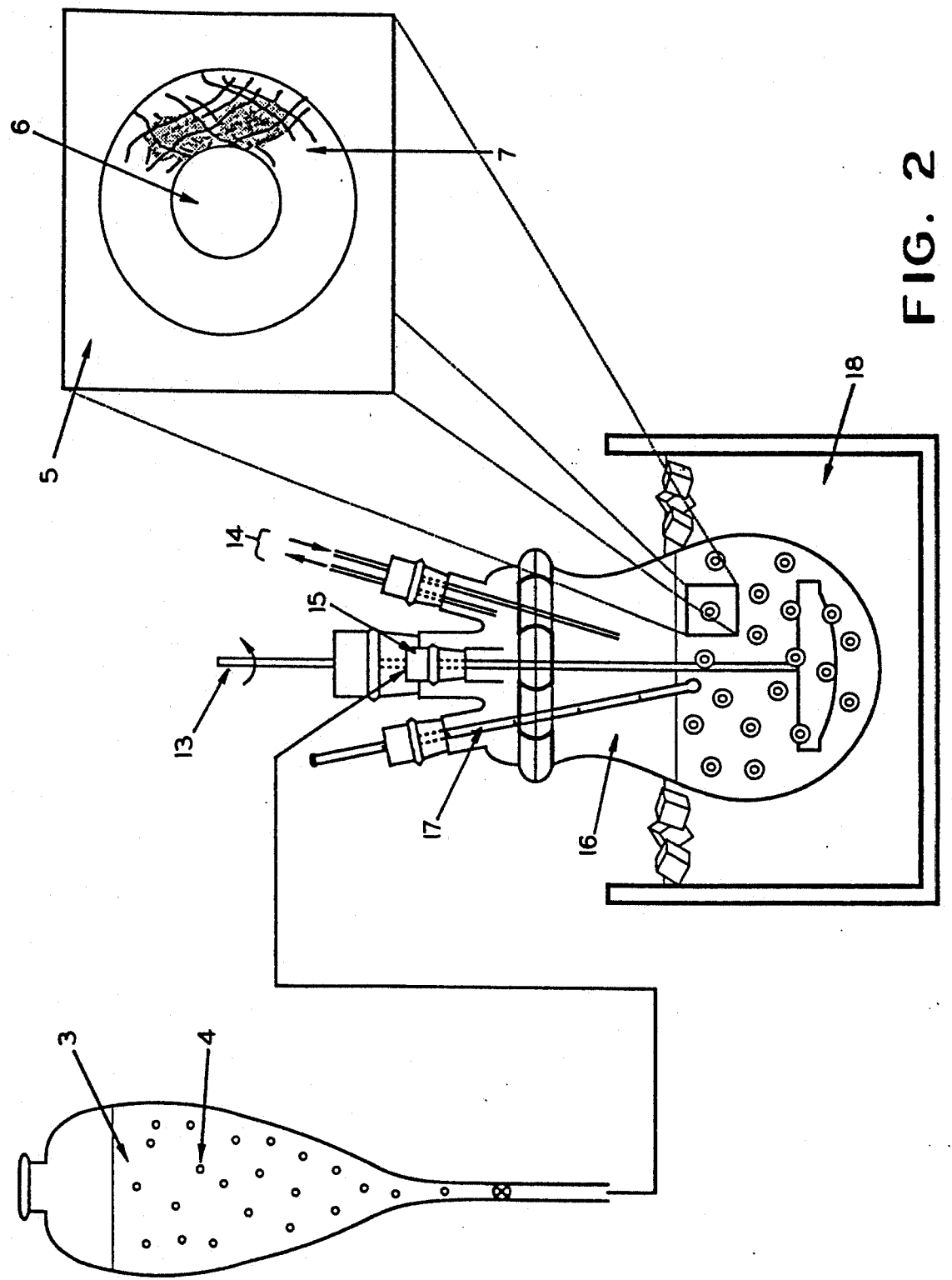
FIG. 2 is a schematic illustration of the process for manufacturing the bilayered pellets described herein.

The above process for manufacturing the bilayered pellets is schematically shown in FIG. 2 for laboratory scale production. In this example, a 3:1 (v/v) mixture of toluene and chloroform forms the hydrophobic phase (5). The surfactant Sorbitan sesquoleate is added to this hydrophobic phase in a 1:8 (v/v) ratio. The hydrophobic phase (5) is placed in a flask (16) having a stirrer (13), $N_2$ inlet and outlet sources (14), an isolable funnel (15), and a thermometer for measuring temperature (17). The flask is kept in an ice bath (18) so as to maintain the hydrophobic phase between 0° to 4° C. The 3:1 ratio of toluene to chloroform leads to an organic phase which has a density approximately equal to that of the aqueous phase. The 1:8 ratio of surfactant to the hydrophobic phase controls the size of the outer layer of the pellet, thus this ratio can be varied to achieve various thicknesses of the outer layer.

The aqueous phase (3) for this example is prepared in the following manner. For each 100 ml of 0.05M triethanolamine - HCl buffer, approximately 15% (w/v) of acrylamide monomer is mixed with approximately 0.5 to 1.0% (w/v) of the crosslinking agent, N,N'-methylenebisacrylamide (BIS) and 60 mg of the enzyme urease. The zone 1 particles (4) are then dispersed within this aqueous phase (3) creating the aqueous suspension, and this suspension is kept chilled until it is desired to begin the polymerization.

When it is desired to begin the polymerization, the polymerization initiators are added to the aqueous suspension and this mixture is then quickly added to the hydrophobic phase contained in a flask (16). In this example, approximately 0.5 ml of N, N, N',N'-tetramethyl-ethylenediamine (TEMED) and 0.25 gm of ammonium persulphate are added as the polymerization initiators. Once the aqueous suspension with the polymerization initiators has been added to the hydrophobic phase, the process is allowed to proceed for approximately 30 minutes. The polymerization results in a pellet having an inner core region (6) and a thin outer layer (7) comprised of crosslinked polyacrylamide and entrapped urease.

Afterwards, the pellets are washed at 0° to 4° C. on a glass filter, first with toluene to remove the chloroform and then with distilled water. These pellets should be kept at 0° to 4° C. until later used in the simultaneous isomerization and fermentation of xylose process of the present invention.

The glucose and xylose feedstocks for use in the present invention are prepared using conventional acid and enzymatic hydrolysis of lignocellulose. Cellulose, which provides the glucose feedstock, is difficult to hydrolyze due to its crystalline structure and its close association with lignin in the biomass. In contrast, the amorphous structure of hemicellulose allows it to be easily hydrolyzed by a weak acid into its constituent sugars, namely xylose, as well as arabinose and glucose.

The yeasts that are suitable for use in the present invention include those strains which can easily ferment both glucose and xylulose Although there are several known yeasts which can ferment xylose directly, the yeasts which can directly ferment xylulose and glucose exhibit a higher ethanol productivity and ethanol tolerance than the xylose fermentable yeasts. The best producers of ethanol from xylulose and glucose are species of Brettanomyces, Sciizosaccharomyces, Torulaspora, Saccharomyces, Paschysolen, Kluyveromyces, Hansenula and Candida. The Saccharomyces species is preferred for use in the present invention because of its high ethanol productivity and ethanol tolerance.

The previously described constituents are utilized in the simultaneous isomerization and fermentation process of the present invention in the following manner. First xylose and glucose feedstocks, urea, yeast cells, and a buffer if necessary, are mixed together in a closed reactor which has agitation means. This mixture, which is primarily comprised of an aqueous solution of xylose and glucose sugars, urea, buffer and suspended yeast cells, will hereinafter be referred to as the bulk liquid. The pH of this bulk liquid should be maintained in a pH range of 4.0 to 5.0, preferably around 4.5.

Urea is used in the present invention for two purposes. First it can be used in the fermentation broth as a supply of nitrogen for the yeast. Typically a concentration of 0.01M maintained in fermentation broth would be appropriate for this purpose. However, the primary use of urea in the present invention is for its hydrolysis to ammonia by the enzyme urease entrapped in zone 2 of the pellet. The ammonia is used to maintain the pH in zone 1 in a range of 7.0 to 8.0, as will be further described below. In order to achieve both these purposes, the concentration of urea in the bulk liquid should be in the order of 0.01M.

The bilayered immobilized enzyme pellets of the present invention are also added to the bulk liquid contained in the reactor. Conventional fermentation techniques, which are well known in the art, are then used to ferment the sugars in the bulk liquid into ethanol. As is typical in the fermentation process, largely anaerobic conditions (small amounts of oxygen may be beneficial) and temperatures between 30° to 40° C. are required for the present invention.

Although the present invention makes use of known isomerization and fermentation techniques, there are several processes occurring as a result of the present invention that allow xylose to be converted to ethanol using yeasts which cannot directly ferment xylose. These processes include:

1) the maintenance of the pH in zone 1 in a range of 7.0 to 8.0;
2) the isomerization of xylose to xylulose under optimum pH conditions for the isomerization reaction;
3) simultaneously with the isomerization process, the fermentation of xylulose and glucose to ethanol under optimum pH conditions for fermentation; and
4) the "pulling" of the xylose to xylulose reaction towards xylulose production by making the newly formed xylulose immediately available for fermentation, and thus overcoming the unfavorable equilibrium constant of the above reaction.

The maintenance process just described is shown in FIG. 1. In this figure the pH of the bulk liquid is designated as $pH_b$ while the pH in zone 1 is designated $pH_o$. Starting from the outer edge of the pellet and moving radially inward, the pH increases monotonically from pH to a higher value $pH_o$ at the interface of zones 1 and 2 due to a reaction that takes place in zone 2 that will be described later. The present invention provides a means which causes the $pH_o$ to be in a range of 7.0 to 8.0, which is the optimum pH range for the xylose isomerization process.

If a batch mode is chosen for use with the present invention, a buffer having a pK of 4.5 could be used to maintain the pH of the bulk liquid in a range of 4.0 to 5.0, preferably at 4.5. Alternatively and when a continuous mode of this process is desired, appropriate acids and/or bases can be used to maintain the pH in this range.

In the present invention, the isomerization and fermentation processes will occur simultaneously but at different locations within the reactor. The isomerization of the xylose to xylulose will occur in zone 1 of the pellet. The xylose will diffuse into the pellets, be isomerized to xylulose by the xylose isomerase, and then the xylulose will diffuse out of the pellet into the bulk liquid. Once the xylulose is in the bulk liquid, it will be fermented by the yeast.

The catalyst for the isomerization process, xylose isomerase, requires a pH of 7.0 to 8.0 to achieve its maximum activity. Initially, the interior of the pellet can be adjusted within this optimum range, but as time progresses, hydrogen ions from the bulk liquid will diffuse into zone 1, lowering the pH and thus inactivating the immobilized enzyme. The present invention precludes this from occurring by immobilizing the enzyme urease in the outer layer (zone 2). The urease will hydrolyze the urea present in the bulk liquid as it diffuses into the pellet, thus forming ammonia. The ammonia in turn will neutralize any hydrogen ions from the bulk liquid as they diffuse into the pellet from the bulk liquid.

The ability of the bilayered immobilized enzyme pellet to maintain a pH gradient between the pH in the bulk liquid and zone i is largely dependent on two factors. These are 1) the thickness of the outer layer of the pellet (zone 2) and 2) the amount of the enzyme urease immobilized in zone 2, also referred to as urease loading. An increase in the thickness of zone 2 increases the diffusional resistance the hydrogen ions in the bulk liquid must overcome in order to reach zone 1. In addition, a larger enzyme loading provides a greater number of reaction sites where the urea can be hydrolyzed to form ammonia. Therefore, either an increase in the thickness of zone 2 or in enzyme loading will result in the pH in zone 1 ($pH_o$) being greater than the pH of the bulk liquid ($pH_b$), thus creating the desired pH gradient The relationship of the above two factors, i.e. the thickness of zone 2 and the urease enzyme loading can be represented by a dimensionless parameter known as the Thiele Modulus. The exact formula for the Thiele Modulus is defined in a University of Toledo Master of Science Degree thesis entitled "A Novel Approach for the Conversion of D-xylose to D-xylulose and its Simultaneous Fermentation Through the Control of the pH Environment in an Immobilized Enzyme System" and in "A Feasibility Analysis of a Novel Approach for the Conversion of Xylose to Ethanol" to be published in Chemical Engineering Communications. These references describe a mathematical model which simulates the steady state behavior of the bilayered immobilized enzyme pellet of the present invention and shows that a pH gradient can be achieved between the pH of the bulk liquid and that found in zone 1. The information contained in these documents is expressly incorporated herein by reference.

Experimental results show that the desired pH gradient where the pH of the bulk is maintained between 4.0 and 5.0 and the pH in zone 1 is maintained between 7.0 and 8.0 can be achieved when the Thiele Modulus is greater than 1.25. This assumes that the urea is present in the bulk liquid in a molar concentration range of 0.0167 to 0.0334M and, that if a buffer is present, it is present in a concentration less than or equal to 0.01M. For a more comprehensive review of these experimental results see a University of Toledo Masters of Science thesis entitled "An Experimental Study of the Generation of a pH Gradient in an Immobilized Enzyme System." which is expressly incorporated herein by reference.

In summary, the bilayered immobilized enzyme pellet of the present invention is able to create a pH gradient which allows the xylose isomerization reaction to occur within its optimum pH range of 7.0 to 8.0 while allowing the xylulose and glucose fermentation to occur within its optimum pH range of 4.0 to 5.0.

The present invention has another advantage in that it tends to "pull" the isomerization process towards the production of xylulose The equilibrium constant for the isomerization reaction is not very favorable (i.e., a ratio of xylulose to xylose of approximately 1:5). Therefore, even under optimum pH conditions for this reaction, a low yield of xylulose would be achieved, unless the xylulose is consumed as soon as possible after it is formed, therefore allowing the isomerization reaction to proceed in forming xylulose. The present invention accomplishes the quick depletion of xylulose by placing the location of the isomerization process within close proximity to the fermentation location. Therefore as soon as the xylulose is formed and diffuses into the bulk liquid, it will be available for the fermentation process, thus "pulling" the isomerization process towards xylulose production.

The invention having been thus described, it will be appreciated that various departures can be made therefrom without departing from the scope thereof. Various changes and modifications may be made from the preferred embodiments described above and still be within the scope and spirit of the appended claims.

What is claimed is:

1. A bilayered immobilized enzyme pellet for use in the simultaneous isomerization and fermentation of xylose to ethanol consisting of in combination:
   a core region consisting of porous polymer material having xylose isomerase immobilized therein and an outer layer consisting of porous polymer material having urease immobilized therein.

2. A pellet as defined in claim 1 in which the outer layer of polymer material is polyacrylamide.

3. A process for the manufacture of a bilayered immobilized enzyme pellet comprising the steps of:

immobilizing xylose isomerase in a porous polymer material so as to form an inner core region of a particle, mixing said particles with water, urease, a monomer, a crosslinking agent, and a polymerization initiator so as to form an aqueous medium, said aqueous medium and particles comprising an aqueous suspension, maintaining said aqueous suspension at a temperature between 0° to 4° C., adding toluene, chloroform, and a surfactant to the suspension so as to form an aqueous hydrophobic phase, agitating said hydrophobic phase under nitrogen conditions and at a temperature between 0° to 4° C. to allow polymerization of said monomer to form a thin polymer coating containing said urease immobilized therein around said particles to form said bilayered immobilized enzyme pellet.

4. A bilayered immobilized enzyme pellet produced by the process of claim 3.

5. A process as defined in claim 3 in which the polymer coating is polyacrylamide.

6. A process for the simultaneous isomerization and fermentation of xylose to ethanol comprising the steps of:

immobilizing xylose isomerase in a porous polymer material so as to form a spherical particle, said particle forming an inner core region of a larger pellet, mixing said particles with water, urease, a monomer, a crosslinking agent, and a polymerization initiator so as to form an aqueous medium, said aqueous medium and particles comprising an aqueous suspension, maintaining said aqueous suspension at a temperature between 0° to 4° C., adding toluene, chloroform, and a surfactant to the suspension so as to form an aqueous hydrophobic phase, agitating said hydrophobic phase under nitrogen conditions and at a temperature between 0° to 4° C. to allow polymerization of said monomer and to form a thin polymer coating containing said urease immobilized therein around said particles to form bilayered immobilized enzyme pellets, mixing xylose feedstock, urea, and yeast cells having high ethanol productivity and ethanol tolerance so as to form a bulk liquid, said bulk liquid being placed in a closed reactor having agitation means, setting and adjusting the pH of the bulk liquid so as to maintain the pH in the range of 4.0 to 5.0, dispersing said bilayered immobilized enzyme pellets in said bulk liquid, diffusing xylose into said inner core region of said pellet, isomerizing said diffused xylose to xylulose by contact with xylose isomerase immobilized in said inner core, diffusing said xylulose out into said bulk liquid, adjusting the pH of the liquid in said inner core region during said isomerizing so as to maintain the pH in the range of 7.0 to 8.0 by diffusing said urea in said bulk liquid into the outer layer of said pellet whereby the urea is hydrolyzed to ammonia by the immobilized urease, said ammonia neutralizing any hydrogen or positively charged ions that diffuse from said bulk liquid into said inner core region of said pellet, agitating said bilayered pellets and bulk liquid under substantially anaerobic conditions and at a temperature and for a sufficiently long period of time so as to allow the fermentation of xylulose to ethanol, said fermenting of xylulose to ethanol occurring contemporaneously with the isomerization of xylose to xylulose.

7. A process as defined in claim 6 in which the polymer coating said particles is polyacrylamide.

* * * * *